United States Patent [19]
Radding et al.

[11] Patent Number: 6,022,684
[45] Date of Patent: Feb. 8, 2000

[54] FUNGAL IPC SYNTHASE ASSAY

[75] Inventors: Jeffrey Radding, Carmel, Ind.; Robert C. Dickson; Robert L. Lester, both of Lexington, Ky.

[73] Assignees: University of Kentucky Research Foundation, Lexington, Ky.; Eli Lilly and Company, Indianapolis, Ind.

[21] Appl. No.: 08/944,594

[22] Filed: Oct. 6, 1997

Related U.S. Application Data

[60] Provisional application No. 60/028,079, Oct. 7, 1996.

[51] Int. Cl.$^7$ .............................. C12Q 1/00; C12Q 1/02
[52] U.S. Cl. .............................. 435/4; 435/29; 435/32; 435/35; 435/15; 435/194
[58] Field of Search .............................. 435/194, 29, 32, 435/35, 15, 4

[56] References Cited

FOREIGN PATENT DOCUMENTS

63129/94   1/1994   Australia .
0 644 262 A2   3/1995   European Pat. Off. .

OTHER PUBLICATIONS

Ko et al. Regulation of phosphatidylinositol:ceramide phosphoinositol transferase in Saccharomyces cerevisiae. J Bacteriol. 1994;176(16):5181–3, Aug. 1, 1994.

Aucott et al. Invasive infection with Saccharomyces cerevisiae: report of three cases and review. Rev Infect Dis. 1990; 12(3):406–11, May 1, 1990.

Heidler et al. The AUR1 gene in Saccharomyces cerevisiae encodes dominant resistance to the antifungal agent aureobasidin A (LY295337). Antimicrob Agents Chemother. 1995;39(12):2765–9, Dec. 1, 1995.

Hashida–Okado et al. AUR1, a novel gene conferring aureobasidin resistance on Saccharomyces cerevisiae: a study of defective morphologies in Aur1p–depleted cells. Mol Gen Genet. 1996;251(2):236–44, May 23, 1996.

Nagiec et al Sphingolipid synthesis as a target for antifungal drugs. Complementation of the inositol phosphorylceramide synthase defect in a mutant strain of Saccharomyces cerevisiae by the AUR1 gene. J Biol Chem. 1997;272(15):9809–17, Apr. 1, 1997.

Becker et al. Biosynthesis of phosphoinositol–containing sphingolipids from phosphatidylinositol by a membrane preparation from Saccharomyces cerevisiae. J. Bacteriol. 1980;142(3):747–54, Jun. 1, 1980.

Lester & Dickson, 26 Adv. in Lipid Res. 253 (1993).

Wells et al., 178 J. Bacteriol. 6223 (1996).

Heidler and Radding, 39 Antimicrobial Agents and Chemotherapy 2765 (1995).

Hashida–Okado et. al., 251 MGG 236 (1996).

Nagiec et al., 272(15) J. Biol. Chem. 9809 (1997).

Primary Examiner—Ponnathapu Achutamurthy
Assistant Examiner—Bradley S. Mayhew
Attorney, Agent, or Firm—Raymond S. Parker, III; Thomas D. Webster

[57] ABSTRACT

The presently-disclosed IPC synthase-inhibitor assays comprise the steps of: (1) expression of the IPC1 gene in a cell; (2) introducing labeled starting substrates for ceramide conversion as well as potential inhibitor(s) of such conversion to the expressed gene product in an environment which allows time and conditions for conversion, and (3) identifying those potential inhibitors which actually inhibit conversion. The present invention also provides methods to determine the ability of a test compound to inhibit fungal growth, comprising the steps of (1) presenting active inositolphosophotidylceramide synthase in a manner such that synthesis of inositolphosphotidylceramide can occur; (2) introducing ceramide and phosphotylinositol, said ceramide or phosphatidylinositol carrying label for identification; (3) subjecting said active inositolphosophotidylceramide synthase, ceramide and phosphotylinositol to ordinary conditions necessary for ceramide conversion to phosphoinositol ceramide; and (4) identifying those test compounds which inhibit ceramide conversion to phosphoinositol ceramide.

17 Claims, 3 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 4307 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GATCTTTCAT CATTGTGACT GCCTAAAATA TCTTTCAAAA TTTCAGGAAT TTCACCGCCC      60

TTCGATGGAA CGATATAAAA ATCCTTCTCG TATCTAGTTT TTGGCTTTAT ACCTGCAATG     120

CGACCTTTGT TTTCCAGGGA GTCTACAACG TCGGCAAAAG TTGTCTTACT TTCACTATCA     180

TTCGAAGGAA ATAATTGGTA TACTAATATA GCTCTAGAGC AAGAAATTTC CTTAAGATAT     240

GGTGCAGCAG TGGTTGTAGG TAAGCGCCCT TCTACATACA GTTTTCCGTC ACCAATGGCT     300

TCCTTGAAAA TATCCCGTCT TAACTTTTGT GAAGCCCCAA TGTAGTTTAG GTAACCTGTA     360

AACTCAAGTC CTAAGCCGGG ATACAAAAAT GCGCAGTTTA AAGATTCTTC GTTGATTATT     420

GTACTTGGGC TGGGTTCTTT CGAAATGGCA TGAGTCTGTT CTATTTTACT CTTATCGCTG     480

TCGATACTGT CAATGTTGTG TAATCTTATG CTGTCTTTTG AGTACAAAAT ATCCTCTTGA     540

GGTTCAGCGA TATCTTCGAT CAGCTCATCA CCCTTGTGGG TCTTAACGTA CATGGGTTTG     600

TCAGGTACCT CCACGATAAA ATTTTCTAAG ATAATCTTAT CCCTTTTCTC TTTAAATTCT     660

TGTAAGTCAG GATTTGCGAG TTCAGATGCG TTCATGTTCA CCAGTTTATT TAAAGGCAAT     720

TTGCCCTCGA CAACGTGTGC CTTCAGTTCC AAATTTTTTT TATCCTTTAA ATTAGAGTAT     780

AACGACCTCA CTTTCTCTGT GTATATCTTG TCCAAAGTAC CAAACTCGAC GTTAAGGCAA     840

GCTTTGTAAA GTTCTTCTTC CAGATTGTGC GCAAACTCTT GCGATATCGA TATAACGTCT     900

TTCCCATCAG GAAGCTCATA AAGTTTTGCC TCAATTGTTT CGGGAACGAT GAATTTGCTA     960

AATAAGGTAG AGAACATTTT TTCTGCATTA TACCTCAGTT TGTGTTCTTT TTCGCTTTCA    1020

AAATCTTTCC TAGTAGGCAT TTCGTTTTCG GCAGTATCAG ACTTGGCGGC ATCAATGCTT    1080

TTATTCCTTT TTTTTGACCC ATTGGATTTC TTCACCTGTT TGGATTTGAT ATGAATTCCT    1140

TTGGCACTAT CGGGGCTCCT TTTTCGTTTC CTAGGGCTTT CCTCATCAAG AAAGACATCT    1200

GCATCATTGT CATCATGGTC ATTTACGGGC TTGTAAACAT CATCATGGTA ATCTTCATCC    1260

TCTGAAACCT CTGCCTCCTT TGACGTTTCC AAATGTGCAT ACAATGATGG GTCGCACAAT    1320
```

```
TCACAGTAGT ACTTAGAATC TTCACTCATT AGCCCATCTA TGGTGTCTTT ACCATCAGTC    1380

ATACATTTAA TATGCTGCCA AGTGTCACAG CCATCGCACT GTACCATGTC GCCATGCGAA    1440

TATTCTGCAG CATCGTAGTT TTCATTGTTC GCCCCACACA GACATCTAAC ATAGCCCTCA    1500

TCCGCTTCGT CTACTTCGTC TGTTCTTACA TTTTCAGTAT CTTTCCTTGG CTCCTGAGAA    1560

GAATCAGACT TCTTATTCTT CTCTATGGCT GAATCAACTT TCTTTTTAGT TCTTTTTTTC    1620

TTTGGTGCTT CAGTCTCCTC CTGTAACAAA TACTCAATAT ATTTATTCTG ACCCTTATTA    1680

GATCTTGAAG AAGTACGGAC AGACATAATA AATTTAAACT AAATAAAAGC TAAAAGTAAA    1740

AGAGAACCTA GGATAATCGA TAGCTCCCTG TGTATAGAAC AAGTCAAAAT ACTAAGATCT    1800

CGTCAACCTA TCCTCTTTCA TTGCAAGCCT TTTGGCCAAA CTGCAGTCTG GCATCCCTT     1860

TGCATGTCTT GTGAAATAGT ATCCATCTCT CCCCAGCTCC CAGAAATGAT ATGAAAAGTT    1920

ATTCGTGAAG AGTGATCCTA AAACTGAAAA AGGAAAAAA CAAAAATGAG CTAAAAAAAC     1980

CACAACAAAA GAATATCAAC TTCATTGCTT GGCGGGTCAT CGCTTTTTTA TTTCTTTCTG    2040

TCAAAGAATA ATAAAGTGCC CATCAGTGTT CATATTTGTT ACAAAGTGGT TTTCTGATTT    2100

GGTACTACTG CAGAGGCGTA TTTTTTGCTT CAGTTACCAT AGCGTAAGAA CACTAGCGAC    2160

TTTTGTTCGT GAACCAACAG AGTAGGATTT CTACTGCTAC ATCTCTTAGG TAGTTGGTTA    2220

GTCCGATCGC TCACTTTTGG TTGTTGTTAA GTACTTCATA AGTTTATCCT TTTCCTTTTT    2280

CACACTGAGC TACTTTGGGT ATAGCTTTTG GCCCAAGGAT CTTTGAATTT CTCCAAAAG     2340

TACTTTATTT TATATCCTAC AGGTTGCGGT TTTCATATTT TAAAAGCTT TTAATCATTC     2400

CTTTGCGTAT GGCAAACCCT TTTTCGAGAT GGTTTCTATC AGAGAGACCT CCAAACTGCC    2460

ATGTAGCCGA TTTAGAAACA AGTTTAGATC CCCATCAAAC GTTGTTGAAG GTGCAAAAAT    2520

ACAAACCCGC TTTAAGCGAC TGGGTGCATT ACATCTTCTT GGGATCCATC ATGCTGTTTG    2580

TGTTCATTAC TAATCCCGCA CCTTGGATCT TCAAGATCCT TTTTTATTGT TTCTTGGGCA    2640

CTTTATTCAT CATTCCAGCT ACGTCACAGT TTTTCTTCAA TGCCTTGCCC ATCCTAACAT    2700

GGGTGGCGCT GTATTTCACT TCATCGTACT TTCCAGATGA CCGCAGGCCT CCTATTACTG    2760

TCAAAGTGTT ACCAGCGGTG GAAACAATTT TATACGGCGA CAATTTAAGT GATATTCTTG    2820

CAACATCGAC GAATTCCTTT TTGGACATTT TAGCATGGTT ACCGTACGGA CTATTTCATT    2880

TTGGGGCCCC ATTTGTCGTT GCTGCCATCT TATTCGTATT TGGTCCACCA ACTGTTTTGC    2940

AAGGTTATGC TTTTGCATTT GGTTATATGA ACCTGTTTGG TGTTATCATG CAAAATGTCT    3000

TTCCAGCCGC TCCCCCATGG TATAAAATTC TCTATGGATT GCAATCAGCC AACTATGATA    3060

TGCATGGCTC GCCTGGTGGA TTAGCTAGAA TTGATAAGCT ACTCGGTATT AATATGTATA    3120

CTACAGCTTT TTCAAATTCC TCCGTCATTT TCGGTGCTTT TCCTTCACTG CATTCCGGGT    3180

GTGCTACTAT GGAAGCCCTG TTTTTCTGTT ATTGTTTTCC AAAATTGAAG CCCTTGTTTA    3240

TTGCTTATGT TTGCTGGTTA TGGTGGTCAA CTATGTATCT GACACACCAT TATTTTGTAG    3300

ACCTTATGGC AGGTTCTGTG CTGTCATACG TTATTTTCCA GTACAAAAG TACACACATT     3360

TACCAATTGT AGATACATCT CTTTTTTGCA GATGGTCATA CACTTCAATT GAGAAATACG    3420

ATATATCAAA GAGTGATCCA TTGGCTGCAG ATTCAAACGA TATCGAAAGT GTCCCTTTGT    3480

CCAACTTGGA ACTTGACTTT GATCTTAATA TGACTGATGA ACCCAGTGTA AGCCCTTCGT    3540

TATTTGATGG ATCTACTTCT GTTTCTCGTT CGTCCGCCAC GTCTATAACG TCACTAGGTG    3600

TAAAGAGGGC TTAATGAGTA TTTTATCTGC AATTACGGAT ACGGTTGGTC TTATGTAGAT    3660

ACATATAAAT ATATATCTTT TTCTTTCTTT TTCTTAGTCA GGATTGTCGT TTAGCATAAT    3720
```

-continued

```
ATACATGTAG TTTATTTAAT CACATACCAC TGATTATCTT TAGAATTTTA TAAATTTTTG    3780

AAATAAATGG GTGGCTTTTA ATGGTGTCTA TGTTAAGTGA GGCTTTTAGA ATGCTCTTCC    3840

TGCTTTGTTT ATTATATGTG TATGAAAGAT ATGTATGTAT TTACATGTGT TTGTAGCGTC    3900

CCCAGTCAAA ACCTGTGCGC TATACCTAAA TGGATTGATA ATCTTCATTC ACTAATTCTA    3960

AAATAGACTT CTTCCCCAAA GAACGGTGTA ACGATGAGGC TCTATCCAGC TGCTTATCTA    4020

AATCAACTTT AACGATGGAT GATCTTATGA CACGGGGATC TTTCTTTAAA GTTCTTAGAA    4080

TTTCAGACTG TACCGCAGCT GATGAATCAA ACAGCATTAA AAAGTGATAT GCTCGAAAAT    4140

GTTTTTCCTG GTCTTTCTTC ATTATTTTAG GAAGATACCT TATGCCCATG GGTACAATGT    4200

CCCTCACCAC ACCTCTGTTT TGAATAATCA GTTTCCCGAT TGTGGAAGAC AATTCTTTTG    4260

CTTCCAACTT TGGCGCATTG GAGTTGGTTA TGCGAACAAG TCCGATC                 4307
```

FUNGAL IPC SYNTHASE ASSAY

This application claims benefit of U.S. Provisional Application No. 60/028,079, filed on Oct. 7, 1996.

BACKGROUND OF THE INVENTION

In sphingolipid biosynthesis of fungi, inositolphosphorylceramide(IPC) synthase is responsible for transferring inositol phosphate from phosphatidylinositol to the fungal ceramide to form inositolphosphorylceramide. The presence of inositolphosphorylceramides have been demonstrated in yeast (*S. cerevisiae*) and in pathogenic fungi (*C. albicans, Aspergillus fumigatus, H. capsulatum*). Lester & Dickson, 26 *Adv. Adv. Lipid Res.* 253 (1993). It is also known that in the model yeast, *S. cerevisiae,* inositolphosphosphingolipids are essential for viability. Wells et al., 178 *J. Bacteriol.* 6223 (1996).

Moreover, although elements of the synthetic pathway for sphingolipids in fungi are shared by mammalian sphingolipid synthesis, the pathway is divergent at the step after formation of ceramide. Martin & Pagano, 159 *Anal. Biochem.* 101 (1986). Thus, inhibitors of IPC synthase are likely candidates for antifungal chemotherapy.

In a copending application, Ser. No. 08/882,767, Dickson, Lester and Nagiec characterized the IPC synthase gene (IPC1). In that application, the DNA sequence of IPC1 is disclosed, as is the corresponding amino acid sequence of the enzyme.

SUMMARY OF THE INVENTION

The present invention relates generally to an assay for inhibitors of IPC synthase. Because this invention makes high-throughput screening of potential inhibitors possible, the identification of lifesaving treatments using the assays disclosed herein is more likely.

In one embodiment of the present invention, the assays comprise expression of the IPC1 gene in a cell, introduction of labeled starting substrates for ceramide conversion as well as potential inhibitor(s) of such conversion to the expressed gene product in an environment which allows time and conditions for conversion, and identifying those potential inhibitors which actually inhibit conversion. Preferably, the labeled starting substrates are radiolabeled, fluorescent or biotinylated derivatives of the fungal ceramide. Moreover, a method for identifying compounds which inhibit IPC synthase by using derivatized analogs of the fungal ceramide as a potential acceptor for the inositol phosphate moiety by fungal IPC synthase is also disclosed.

DETAILED DESCRIPTION OF THE INVENTION

Figure 1:
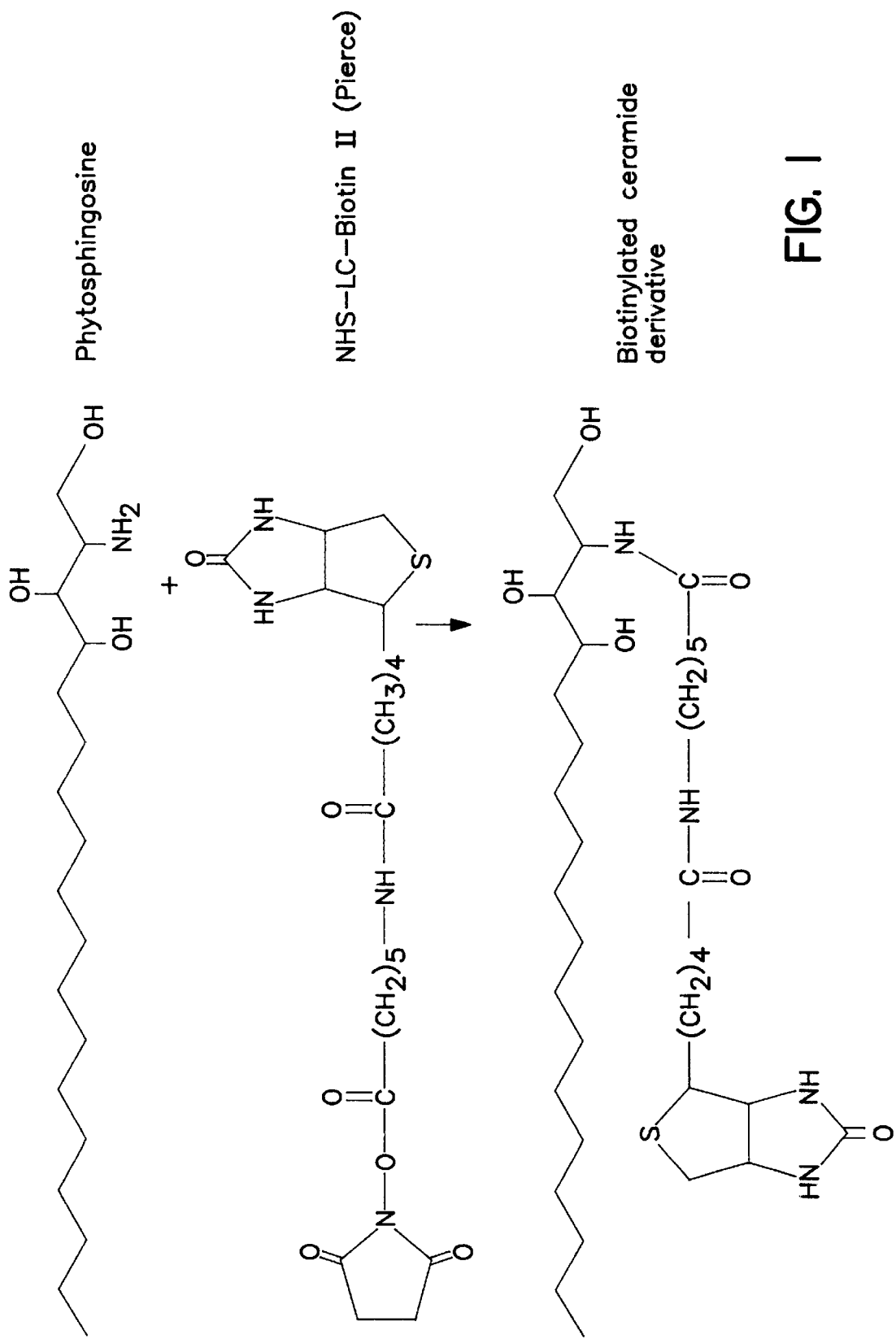
FIG. 1 Synthesis of biotinylated fungal ceramide derivative.

The presently-disclosed IPC synthase-inhibitor assays comprise the steps of (1) expression of the IPC1 gene in a cell; (2) introducing labeled starting substrates for ceramide conversion as well as potential inhibitor(s) of such conversion to the expressed gene product in an environment which allows time and conditions for conversion; and (3) identifying those potential inhibitors which actually inhibit conversion. In one embodiment, the IPC1 gene is overexpressed so as to provide excess available IPC synthase. In order to transfect and/or overexpress the IPC1 gene, one in the art can use conventional methods (ie. J. Sambrook et al., Chapter 16, *Molecular Cloning: A Laboratory Manual,* 2d ed., Cold Spring Harbor Press (1989)) and the materials disclosed in Example 2.

Expression of the IPC1 gene can take place in any known cell line which is capable of expression of genes. Preferred cell types include *E. coli, S. cerevisiae* and *S. pombe.* However, human pathogenic fungal cells may also be used, including, for example, *C. albicans, C. parapsilosis, C. glabrata, C. tropicalis, C. krusei, A. fumigatus, A. flavus* and *C. neoformans.* Moreover, any expression vectors are useful in the present invention, but vectors useful to overexpress the gene are preferred. For example, the baculovirus expression system is useful in the present invention. Summers & Smith, *Texas Agric. Exp. Stn. Bull.* 1555 (1987). In addition, preferred vectors include: pYX212; pYX213; pYX012; pYX013; YEp 24 and Yrp7. These vectors can be commercially obtained. The first four in the list can be obtained from Novagen. YEp 24 is available from American Tissue Type Culture Collection (ATCC) under Accession Number 37051. Yrp7 was disclosed in Struhi et al., 76 *Proc. Nat. Acad. Sci.* 1035 (U.S.A. 1979). Regulatory or cis-regulatory sequences of the expression vector are preferably those useful for overexpression as well. For instance, those that have galactose-inducible promoters are most preferred.

The starting substrates useful for the present invention can be any ceramides which are capable of being converted from the ceramide to the inositolphophorylceramide and are capable of being labeled. In particular, $C_2$–$C_{12}$ ceramides are preferred for use in this assay. In particular, NBD-$C_6$-ceramide and BODIPY-$C_5$-ceramide are useful in this invention. The label can be on either the PI or the ceramide substrate. Moreover, N-hexanoyl-sphingosine appears to be an effective substrate for IPC synthase. R groups on N-hexanoyl-sphingosine can be biotin, 4-nitrobenzo-2-oxa-1,3 diazole (NBD), 8-methyl-4,4-difluoro-1,3,5,7-tetramethyl4-bora-3a,4a-diaza-3-indacene (BODIPY), or any other small molecule hapten which an antibody can recognize. Any other fluorescent moiety can also substitute for NBD or BODIPY.

Radioactive materials, in particular tritium or radioactive phosphorous, such as $^{32}P$ or $^{33}P$, or carbon, such as $^{14}C$, or fluorescent materials are useful in the present invention. Radiolabeled and chromogenic substrates are commercially available from Amersham (2636 South Clearbrook Drive, Arlington Heights, Ill., 60005 (800-341-7543)) or Dupont New England Nuclear (1007 Market Street, Wilmington, Del. (800-441-7515)) and Molecular Probes, Inc. (P.O. Box 22010, Eugene, Oreg. 97402-0469 (800-438-2209)), respectively. Substrates can be labeled by any useful means. Those in the art recognize that many fluorescent markers and probes can be used, and are aware of the methods to make such markers and probes. Typical materials and means for labelling are described in Martin and Pagano, 159 *Anal. Biochem.* 101 (1986).

Figure 2:
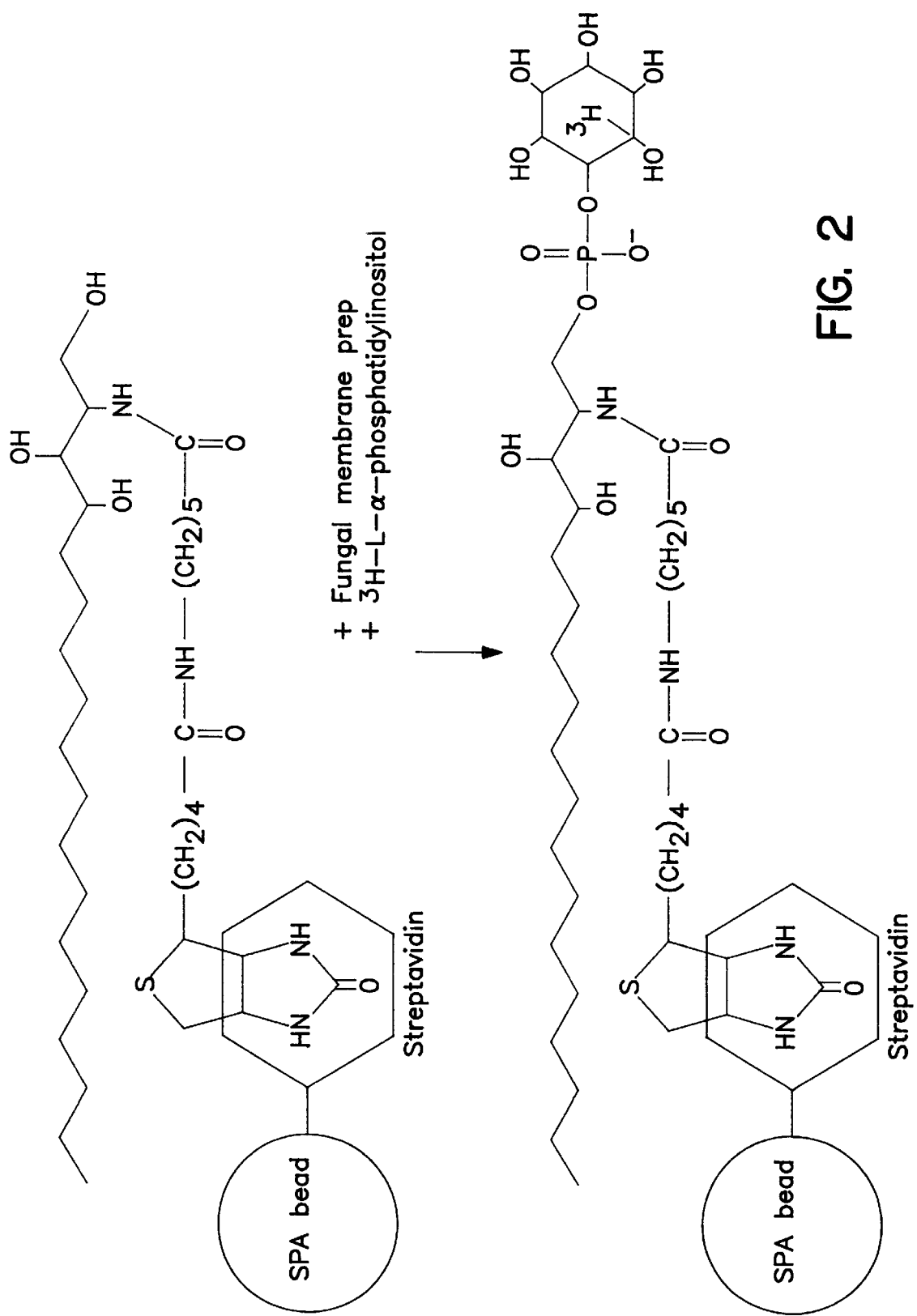
FIG. 2 Schematic SPA assay for IPC synthase using biotinylated fungal ceramide.
Figure 3:
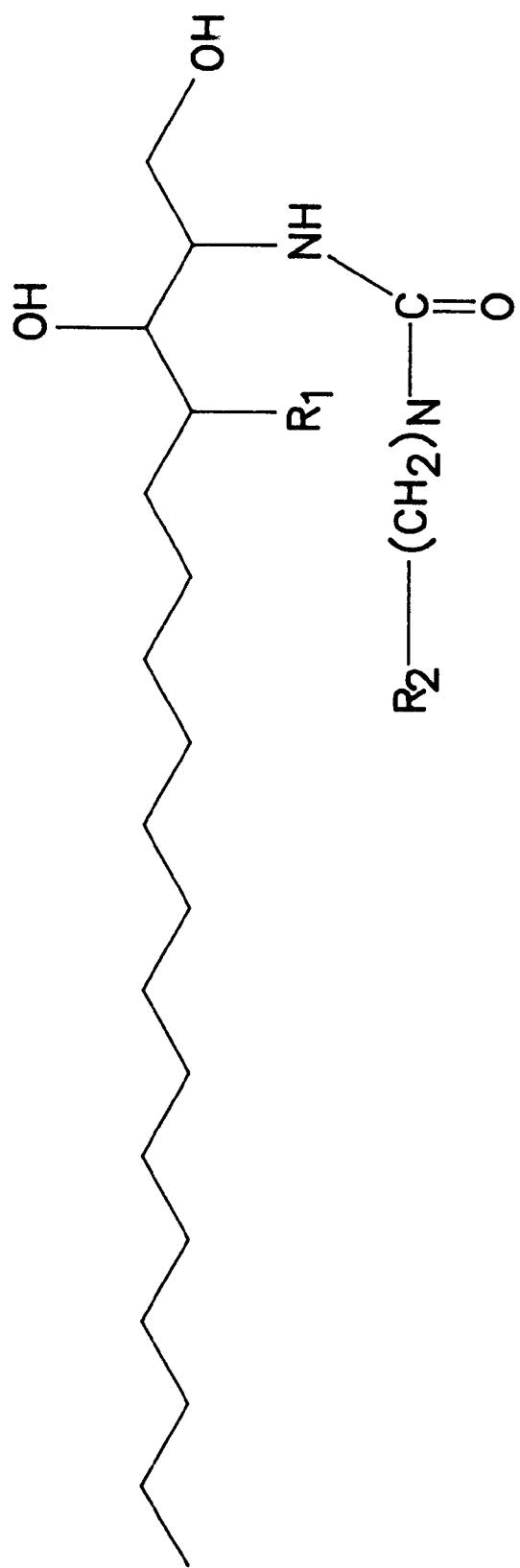
FIG. 3 Derivatized Ceramide Analogues Useful for IPC Synthase Assays

In another embodiment of the invention, phytosphingosine (available from Sigma) can be derivatized with biotin by acylation of the free amine with a biotinylated spacer arm. This procedure provides an analog of the fungal ceramide with a molecular handle (FIG. 1). The analog can then be used as an acceptor molecule and conjugated (pre-reaction or post reaction) to streptavidin derivatized solid substrate such as SPA beads or derivatized affinity chromatography materials for separation of radio-labeled ceramides. Reaction with tritiated phosphatidylinositol as the donor would result in scintillation of the SPA by proximity of the newly derivatized ceramide (FIG. 2). Alternatively, labeled streptavidin bound to biotinylated conversion product can be filter-separated. Also, antibodies can be used to identify hapten-labeled conversion products.

Conditions for conversion can be any of those known in the art, and can be in vivo or in vitro. One preferred condition is the use of crude or purified membrane preparations, incubated according to Becker and Lester, 142 *J. Bactetiol.* 747 (1980) and Ko et al., 176 *J. Bactetiol.* 5181 (1994).

Prior to the present invention, it was not known that inositolphosphotidyl synthase was an essential enzyme for fungal growth. That is, although the activity of IPC synthase was known, it was not known that a cell lacking in IPC synthase activity would not grow. Therefore, the present invention provides methods for determining a compound's ability to inhibit fungal growth. In particular, the present invention provides a method to determine the ability of a test compound to inhibit fungal growth, comprising the steps of (1) presenting active inositolphosophotidylceramide synthase in a manner such that synthesis of inositolphosphotidylceramide can occur, (2) introducing ceramide and phospsphotylinositol, said ceramide or phosphatidylinositol carrying label for identification; (3) subjecting said active inositolphosophotidylceramide synthase, ceramide and phosphotylinositol to ordinary conditions necessary for ceramide conversion to phosphoinositol ceramide; and (4) identifying those test compounds which inhibit ceramide conversion to phosphoinositol ceramide.

Preferred methods to determine a compound's ability to inhibit fungal growth are those wherein the active inositolphosophotidylceramide synthase is presented either as a whole cell culture or a membrane preparation from a human pathogenic fungal cell culture. However, any fungal cells are useful in the present invention. The strains that are particularly easy to grow and maintain in a laboratory setting are preferred for these methods. Certain human fungal cells are listed here to exemplify the human fungal strains which may be used in the present inventive method: *C. albicans, C. parapsilosis, C. glabrata, C. tropicalis, C. krusei, A. fumigatus, A. flavus* and *C. neoformans*.

EXAMPLES

Example 1

IPC1 Complementation of IPC Synthase Defect by IPC1

A. Identification of IPC1 defective cell.

Strains, plasmids, and culture conditions: *S. cerevisiae* strains are: 7R6 (MATa ura3-52 leu2-3,112 lcb1::URA3 SLC1-1 ade1) (Dickson et al., 10 *Mol. Cell. Bio.* 2176 (1990)) which was derived from wild type strain SJ21R (MATa ura3-52 leu2-3,112 ade1); YPH250 (MATa ura3-52 lys2-801$^{amber}$ ade2-101$^{ochre}$ trp-$\Delta$1 his3-$\Delta$200 leu2-$\Delta$1) (available from the ATCC, and useful to make the other strains, by common means); AG27-61 (MATa ura3-52 leu2-3,112 lcb1::URA3 SLC1-1 ade1 lys2-801$^{amber}$ ipc1-1) was derived from 7R6 by the procedure described below. pRS315 is a standard yeast vector and described in Sikorski et al., 122 *Genetics* 19 (1989).

Yeast were grown on modified PYED (bufferred to pH 5.0, PYED-5.0) which contained 1% yeast extract (Difco), 2% Bacto Peptone (Difco), 2% or 4% glucose, 50 mM sodium succinate (pH 5.0), inositol (50 mg/liter), and potassium phosphate monobasic (50 mg/ml (Buede et al., 173 *J. Bactetiol.* 7180 (1991)), or on defined medium supplemented as described (Buede, ibid) and containing, when necessary, 25 $\mu$M (or other indicated concentration of) phytosphingosine (PHS). PYED buffered to pH 4.1 (PYED-4.1) was made by mixing 290 ml of autoclaved agar (2% for plates only), 300 ml of autoclaved yeast extract (1%) plus peptone (2%), 100 ml of filter sterilized glycine (0.5 M, pH 3.1), 200 ml of glucose (20%), 10 ml of inositol (0.5%), and 100 ml of potassium phosphate monobasic (0.5%). The pH was 4.1.

A diploid version of strain AG27-61 (termed AGD27-61) was made by transforming haploid cells with a plasmid (pHO-12 (Russell et al., 6 *Mol. Cel. Bio.* 4281 (1986)) carrying the HO endonuclease gene, responsible for switching of the mating type. Leu$^+$ transformants were streaked onto PYED plates and colonies containing MATa/MATalpha diploid cells were identified by their large, ellipsoidal morphology. Diploids were screened on defined medium lacking leucine for Leu- cells, indicating loss of the plasmid carrying the HO gene, and tested for transformation efficiency using pRS315 (LEU2 CEN4).

Genomic DNA library

A recombinant DNA library containing about 160,000 plasmids, 95% of which carried an insert, was constructed. Genomic DNA from derivatives of strain 4R3 resistant to pH 4.1 was isolated, pooled, and 10 $\mu$g was partially digested with Sau3AI. DNA fragments of 5 to 10 kb were isolated from an agarose gel and ligated with 1 $\mu$g of BamHI-digested, alkaline phosphatase-treated pRS315. Ligated DNA was purified using GeneClean (Bio101, LaJolla, Calif.), electroporated into *E. coli* XL1-Blue cells (Stratagene, LaJolla, Calif.), and plasmid DNA was prepared from ampicillian-resistant colonies selected on petri plates.

Miscellaneous reagents

For some experiments, the agar in petri plates was replaced with agarose (Fisher, BP160-500). pIPC1 is a plasmid isolated from the recombinant DNA library described above in which the 4307 base pair insert corresponds to *S. cerevisiae* Chromosome XI between coordinates 432,813 and 437,119 as described in the *Saccharomyces cerevisiae* genome database at Stanford University (http://genome.www.stanford.edu).

Isolation of strain AG27-61

Strain 7R6 was grown overnight in PYED plus 25 $\mu$M PHS (referred to here as the medium) and then mutagenized with ethylmethanesulfonate to give 20% killing as described in Pinto et al., 174 *J. Bactetiol.* 2565 (1992). Mutagenized cells were diluted to an absorbance at 600 nm ($A_{600}$) of 0.4 with medium, incubated with shaking at 30° C. for 7 h, during which time the $A_{600}$ increased to 2.5, centrifuged, resuspended in 2 ml of medium and sonicated using a microtip (Heat Systems-Ultrasonic) for 2 min to disrupt clumped cells. One ml of cells was layered on 4 ml of 30% sodium diatriazoate (see Pinto et al., 174 *J. Bacteriol.* 2565 (1992)) and centrifuged at 10° C. in a Sorvall RT6000B centrifuge for 4 min at 2000 rpm. Most cells were at the interface but a faint pellet of dense cells was present at the bottom of the tube. The liquid was aspirated and the cell pellet was carefully resuspended in 0.5 ml of medium to avoid mixing with cells stuck to the side of the tube. Resuspended pellets from two tubes were mixed and re-centrifuged on 30% sodium diatriazoate. The cell pellet was resuspended in medium and about 500 cells were spread on PYED plates containing 25 $\mu$M PHS. Two days later only about 15 colonies per plate were visible, suggesting only 3% of the dense cells were viable.

Putative mutants were screened to differentiate those specifically defective in sphingolipid synthesis from those defective in other lipid biosynthetic pathways which might also affect cell density. The screen was based upon the observation that strain 7R6 cannot grow at low pH when it lacks sphingolipids (no PHS present in the medium) but can grow when allowed to make sphingolipids (PHS present in the medium, Patton et al., 1992, J. Bacteriol. 174:7180–7184). Thus, about one hundred mutants unable to grow on PYED plates at pH 4.1 either in the presence of 25 mM PHS were identified.

Mutant strains were examined further for a defect specific to sphingolipid synthesis relative to glycerophospholipid synthesis by looking for decreased incorporation of [3H]-inositol-containing sphingolipids relative to phosphatidylinositol (Zweerink et al. 1992 J. Biol. Chem. 267:25032–25038). By this assay, strain AG27-61 appeared to be specifically defective in sphingolipid synthesis.

[$^3$H]N-acetylsphinganine labeling of sphingolipids in vivo

Cellular conversion of [$^3$H]N-acetylsphinganine to IPC was measured as follows. PYED medium was added to tubes containing solid [$^3$H]N-acetylsphinganine (860 cpm/pmole) and the mixture was dissolved by treatment for five minutes in an ultrasonic water bath. Log phase cells, grown in PYED medium, were centrifuged, suspended in fresh medium and added to the radiolabeled medium to give a final cell density of 1.5 $A_{600}$ units/ml. The final concentration of N-acetylsphinganine was 5.0 $\mu$M. At the indicated times, 1 ml samples were removed, quenched with trichloroacetic acid, and processed as in the inositol-labeling procedure.

Qualitative analysis of 25 $\mu$l samples was carried out on 20 cm Whatman HP-K plates developed with chloroform:methanol:4.2N NH$_4$OH (9:7:2). Each lane contained 2 nmoles of IPC-3 (IPC with a monohydroxylated fatty acid, 2) internal standard. Radioactivity was measured by using a BioScan apparatus and the plates were sprayed with a 10% solution of CuSO$_4$.5H$_2$O in 8% H$_3$PO$_4$ and charred at 160° C. to locate the IPC-3 standard.

Quantification of radioactive products was achieved by ascending chromatography of 5 $\mu$l samples on Whatman SG-81 paper washed with ethylenediamine tetraacetate (see Steiner and Lester, 260 BBA 222 (1972)) and developed with chloroform methanol:4.2N NH$_4$OH (9:7:2). The lanes were cut into one cm zones and counted in a liquid scintillation spectrometer.

In vitro assay of IPC synthase

The inventors elected to develop a less time consuming assay for measuring IPC synthase activity than the published assay which uses chromatography to separate radiolabeled substrate from product, IPC (Becker and Lester, 142 J. Bacteriol. 474 (1980), Ko et. al., 176 J. Bacteriol. 5181 (1994)). The improved procedure separates the substrate and product by differential solvent extraction. A substrate mixture containing 50,000 cpm of [$^3$H]N-acetylsphinganine and 20 nmoles of N-acetylsphinganine, was added to a plastic tube, and dried using a stream of N$_2$. The dry mix was suspended in 50 $\mu$l of 0.2 M potassium phosphate, pH 7.0, 20 $\mu$l of 20 mM CHAPS (Sigma), 40 $\mu$l of 5 mM aqueous phosphatidylinositol, membranes, and water to 200 $\mu$l total volume. Typically 75–300 $\mu$g of membrane protein were added per reaction. The membrane proteins were prepared according to Pinto et al., 174 J. Bacteriol. 2575 (1992), except that the buffer contained 1 $\mu$g/ml of leupeptin, pepstatin and aprotinin and, in addition, the cells were shaken with glass beads for 6 thirty second intervals with a 2 minute period for cooling on ice between the intervals. The reaction mixture was sonicated for 1 min in an ultrasonic water bath before addition of membranes and then incubated for 15 or 30 min at 30° C. with gentle shaking. The reaction was stopped by addition of 2.8 ml of 96.43% methanol (final methanol concentration of 90%). After standing for 10 min the mixture was centrifuged at room temperature. Two ml of the supernatant fluid were mixed with 4 ml of tert-butyl methyl ether (Sigma-Aldrich, HPLC grade), then with 2 ml of water, followed by vortexing, and centrifugation. The lower phase containing the product of the reaction was extracted twice more with 4 ml portions of mock upper phase, prepared by mixing 2 parts of reaction mixture (lacking N-acetylsphinganine, phosphatidylinositol, and membranes) with 4 parts of tert- butyl methyl ether plus 2 parts of water. The volume of the lower phase was measured, and 1 ml was added to 4 ml of scintillation cocktail and counted in a liquid scintillation spectrometer. The cocktail contained 4 gm/l of 2-(4'-t-butylphenyl)-5-(4'-biphenylyl)-1,3,4-oxadiazole, 3 gm/l of 2-(4'-biphenylyl)-6-phenylbenzoxazole, 33.3% Triton X-100, and 66.7% toluene. IPC synthase activity was expressed as pmoles of IPC made/min/mg protein.

Alternative in vitro assay for IPC Synthase—the filter-binding assay

This assay is based on the difference in charge between the substrate for IPC synthase, N-acetylsphinganine (uncharged) and the product, IPC (negatively charged). Test reactions were performed to determine if the charge difference between substrate and product could be the basis for an assay procedure. The test reactions showed that N-acetyl-[3H]sphinganine-P-Inositol (IPC) binds tightly to the following anion-exchange filter papers (all made by Whatman): AE30, aminoethylcellulose; AE81, aminoethylcellulose; and DE20, diethylaminoethylcellulose. An enzyme reaction mixture was prepared in a volume of 100 $\mu$l to give these final concentrations: 100 mM TRICINE (pH 8.1), 0.02% Tergitol, 1 mM phosphatidylinositol, 100 $\mu$g of membrane protein, prepared as for the in vitro assay of IPC synthase described above. The reaction also contained either N-acetyl [3H]sphinganine (152550 cpm, 67 pmoles) or N-acetyl-[3H] sphinganine-P-Inositol (251700 cpm, 110 pmoles). The reaction was immediately quenched by adding 9 volumes of 95% ethanol. Samples (20 $\mu$l) were applied to 2.3 cm diameter DE20 and DE81 filters and air dried. The filters were washed with 95% ethanol and radioactivity was measured by counting in a liquid scintillation spectrometer. The results are shown below:

|  | DE20 (% Original Radioactivity on Discs) | DE81 (% Original Radioactivity on Discs) |
| --- | --- | --- |
| N-acetyl-[3H]sphinganine-P-Inositol | 109 | 90.4 |
| N-acetyl[3H]sphinganine | 2.6 | 1.4 |

These data demonstrate that the substrate N-acetyl[3H] sphinganine barely binds to the filter paper under the solvent conditions used, while the charged product N-acetyl-[3H]

sphinganine-P-Inositol binds very well. These results provide a simple and fast assay for IPC synthase enzyme activity.

Preparation of [4,5-$^3$H]N-Acetylsphinganine

N-acetylsphingosine Matreya, Inc.) was reduced in ethanol with Tritium gas (American Radiochemicals, Inc.) in the presence of Adams catalyst. The sample was dried, dissolved in 0.2 ml chloroform, and applied to a 0.5×50 cm column of Adsorbosil (100/200 mesh) prewashed with chloroform:methanol (1:1) and equilibrated with chloroform. The elution schedule was: 14 ml of chloroform followed by chloroform-methanol (97:3), collecting 7 ml fractions. Fractions 11–16 were pooled, dried, dissolved in methanol, applied to silica gel thin layer plates (Whatman LK5) and developed with chloroform:methanol (95:5). The appropriate zone, located by autoradiography, was scraped and transferred to a syringe fitted with a Teflon filter (Acro LC3S, 0.45µ, Gelman Sciences, Inc,). The [$^3$H]N-acetylsphinganine was eluted with 8 ml of methanol. The thin layer chromatography step was repeated. The final product, with the same mobility as authentic N-acetylsphinganine prepared according to a published procedure (Gaver and Sweeley, 88 *J. Am. Chem. Soc.* 3643 (1966)), had a specific activity of $1.5 \times 10^7$ dpm/nmole.

Miscellaneous procedures

Yeast were transformed using LiOAc-treated cells (Gietz et. al., 8 *Nucleic. Acids. Res.* 1425 (1992)). Protein concentration was determined with the Bradford reagent using bovine serum albumin as standard (BioRad Inc.).

B. Isolation of the IPC1 gene.

A gene that complemented the defect in AG27-61 could not be isolated directly from the haploid because the strain transformed at too low a frequency, about one transformant per microgram of plasmid DNA. Since diploid yeast strains are generally more vigorous, a diploid version of AG27-61 was examined and found to be transformed at a high enough frequency to allow screening of a recombinant DNA library. One diploid strain, designated AGD27-61, was transformed with a recombinant DNA library carried in pRS315. A pool of about 3000 Leu$^+$ transformants was treated with 10 µM phytosphingosine (PHS) to enrich for the desired transformant. The rationale for this treatment was based upon the observation that AG27-61 cells die rapidly when treated with 10 µM PHS at a low cell density in defined medium. Following PHS treatment, transformants were spread at various densities on petri dishes containing defined medium lacking leucine, agarose in place of agar, and 10 or 20 µM PHS. Agarose was used in place of agar to enhance the effective concentration of PHS which appears to bind to components in regular bacterial agar. PHS-resistant colonies were obtained from cells transformed with the genomic library but not from an equal number of cells transformed with the vector.

Plasmid DNA from four PHS-resistant colonies was rescued in *Escherichia coli*. The four plasmids, termed pIPC1, gave the same EcoRI restriction fragment pattern, indicating that they carry the same genomic DNA region. Each of the four pIPC1 DNA samples gave transformants when retransformed into AGD27-61 and selected on defined medium lacking leucine and containing 1 or 12 µM PHS whereas AGD27-61 transformed with the vector pRS315 gave no PHS-resistant transformants at the higher PHS concentration. These data show that the PHS-resistance phenotype is carried on pIPC1.

The sphingolipid synthesis defect in AG27-61 cells, haploid or diploid, prevents them from growing on PYED plates having a pH of 4.1 (PYED-4. 1) when PHS is present whereas the parental strain 7R6 is able to grow because it makes sphingolipids. If pIPC1 restores sphingolipid synthesis then AGD27-61 cells transformed with the plasmid should behave like 7R6 cells and grow on PYED-4.1 plates containing 25 µM PHS. (According to Patton et al., 174 *J. Bacteriol.* 7180 (1992). This expectation was fulfilled by all 30 AGD27-61 transformants tested while cells transformed with the vector did not grow. These data indicate that pIPC1 carries a gene that complements the IPC synthase defect in AGD27-61 cells and restores sphingolipid synthesis when cells are fed PHS.

To identify the genomic region carried in pIPC1, the nucleotide sequence at the ends of the genomic insert was determined and used to search the Saccharomyces genome database (http://genome.www.stanford.edu). This search identified a region of 4307 bases located on Chromosome XI between coordinates 432,813 and 437,119. There is only one complete open-reading frame (YKL004w, AUR1) in this interval, which is shown in SEQ ID No:1.

As shown in the following examples, AUR1 encodes IPC synthase. The gene has been renamed IPC1.

C. The IPC1 gene restores IPC synthase activity to AG27-61 cells.

Membranes were prepared from the control parental strain 7R6 and from AG27-61 cells transformed with pIC1 or with a control vector (pRS315) and assayed for IPC synthase activity. Membranes from AG27-61 cells transformed with pIPC1 contained more IPC synthase activity than did the membranes from the 7R6 positive control cells (Table 1). Membranes from AG27-61 cells transformed with pRS315 contained barely detectable enzyme activity (Table 1).

TABLE 1

| Strains | IPC Synthase activity (pMoles/min/mg protein) |
| --- | --- |
| 7R6 | 103 ± 19 |
| AG27-61/pIPC1 | 159 ± 9 |
| AG27-61/pRS315 | 0.2 ± 0.07 |

Restoration of IPC synthase activity by pIPC1 was also examined by using an in vivo labeling procedure in which cells were incubated with a membrane-permeable ceramide, [$^3$H]N-acetylsphinganine, to radiolabel sphingolipids, specifically IPC. The concentration of radiolabeled IPC increased in an almost linear fashion over the 3 hour course of the experiment in A27-61 cells transformed with pIPC1 and, thus, these cells behave like the positive control cells, 7R6 transformed with pRS315, whereas AG27-61 cells transformed with pRS315 showed no synthesis of radiolabeled product (FIG. 2). The data presented in Table 1 and FIG. 2 demonstrate that pIPC1 carries a gene that restores IPC synthase activity to AG27-61 cells.

Example 2

Initial Results from IPC Synthase Assay from *C. albicans*

Using protocol similar to the procedure described by Ko et al., 176 *J. Bacteriol.* 5181 (1994)., except that membranes from *C. albicans* at a concentration of 25 micrograms per reaction, and exogenous C6 ceramide, at a concentration of 0.2 millimolar, with tritiated phosphatidylinositol (Amersham) in a reaction volume at 100 microliters at 30 degrees centigrade at 2 hours the following results were obtained: Reaction conditions indicated incorporation of tritiated phosphoinositol into the C6 ceramide and was inhibited by addition of R106-1 (also known as Aureobasidin A) at 20 micrograms per ml. (R106-1 is disclosed by Takesako et al. 44(9) J. Antibiot. 919 (1991) and Ikai et al., 44 (9) J. Antibiot. 925 (1991).

Example 3

IPC Synthase Assay: FLUOR Method

Strains YPH1wt and SH2-3B AUR1R were inoculated into YEPD (5 ml) supplemented with 20 µg/ml inositol and grown overnight at 30° C. with shaking. Precultures were then inoculated into 250 ml of YEPD+20 µg/ml myo-inositol and grown overnight at 30° C. with shaking. Cells were harvested at between $5 \times 10^7$ cells/ml by centrifugation at 2000×g for 10 minutes. Cells were resuspended in ice-old 50 mM potassium phosphate buffer, pH 7.0 and transferred to a 50 ml conical tube. The cells were then washed twice with ice-cold 50 mM photassium phosphate buffer, pH 7.0.

The cells were then resuspended as a slurry in 5–10 ml of cold 50 mM potassium phosphate, pH 7.0, containing 5 mM DTT, 1 µg/ml aprotinin, 0.6 µMleupeptin, 1 mM PMSF and 1 µg/ml peptatin A. The buffer with protease inhibitors was made fresh just before use and kept cold.

Next, the slurry was tranferred to 2 ml tubes (Mini-beater tubes) and the cells were pelleted by centrifugation at 2000×g for five minutes at 4° C. This was repeated until the packed cell volume was 50% of the tube volume or greater, but less than 75%. The remaining supernatant was removed and 500 µmglass beads were added to the top of the tube. To this was added 50 mM potassium phosphate, DTT and protease inhibitors to fill up the remaining volume. The vial was sealed with a screw cap.

The cells were then disrupted in a Mini-bead beater for 30 seconds, five times with 2–5 intervals on ice for cooling. The disrupted cell paste was separated from the glass beads by filtering through glass wool into a chilled centrifuge tube on ice. The beads are rinsed with cold buffer which was pooled with the original filtrate. The centrifuge tube was then centrifuged at 2000×g for ten minutes at 4° C. to remove cell debris.

The supernatant was transferred to an ultracentrifuge tube and the membranes were pelleted by centrifugation at 100,000×g for sixty minutes at 4° C. The supernatant was discarded and the pellet resuspended in cold buffer, DTT and protease inhibitors and reharvested by ultracentrifugation a second time. The final membrane pellet was resuspended in a minimal volume of cold buffer, DTT and protease inhibitors and then transferred to a chilled dounce homogenizer. The membranes were homogenized with 5–6 strokes of a pestle on ice. The membranes were then diluted with 1/3 volume of glycerol (final 33%) glycerol) and mixed well by inversion. Aliquots were then placed in screw cap microfuge tuges and frozen on dry ice/ethanol and stored at −80° C.

2× master mix was prepared using the following recipe and with the following consituents, to give as final concentrations in the reaction:

| | |
|---|---|
| NBD-$C_6$-ceramide (Molecular Probes) | 5 µM |
| phosphatidylinositol (Sigma - soybean) | 1 mM |
| CHAPS | 2 mM |
| potassium phosphate buffer, pH 7.0 | 50 mM |
| Organic Co-solvent | up to 2.5% |
| (non-specific) protein concentration | 0.45 mg/ml |
| Final Volume | 100 µl |

To the above solution, 46 µl NBD-$C_6$-ceramide (0.1 mg/ml in MeOH) and 142 µl phosphatidylinositol (10 mg/ml in $CHCl_3$) were added, and the product dried in vacuo.

The dried product was then redissolved by adding the following ingredients in the following order: 160 µl 20 mM CHAPS, 560 µl deionized water, 80 µl 0.5 M KPi buffer, pH 7.0 and sonicated for 5 minutes. This was considered "2× master mix".

Membrane stock was thawed and diluted to 1.8 mg/ml in 0.05 M KPi buffer, pH 7.0 and kept on ice.

Reaction Conditions

50 µl of 2× master mix was aliquoted into screw-cap microfuge tubes and kept at room temperature. 20 µl of 0.05 M KPi buffer pH 7.0 was added to each sample, followed by 5 µl of test compound or extract in 50% (max) organic co-solvent. The reaction was initiated by adding 25 µl of membrane stock to each reaction vessel, mixing, and incubating at room temperature for 15 minutes.

Reactions were terminated by addition of 900 µl of ice cold absolute methanol. Samples were then stored at −20° C. for at least one hour and then centrifuged at 14,000×g at 4° C. for 30 minutes. Fluorescence levels were measured using the FLUOR method: RP-HPLC:

| FLUOR Method |
|---|
| Column: Beckman Ultrasphere-ODS |
|     5 um, 150 × 4 mm |
| Buffer: 87% MeOH/13% 50 mM TEAP pH 5.85 |
| Flow: 1 ml/min |
| Temp: Room temp |
| Detector: Beckman Model 157 Fluorescence detector |
|     excitation: 475 nm |
|     emmission: 520 nm |
| Analysis time: 12 min. |

Procedure

100 µl of reaction supernatant was placed in an HPLC microvial. 25 µl of reaction mixture was injected and the chromatogram developed isocratically. Calculation was performed as % product formed:

$$\% \text{ Product formed} = ([NBD\text{-}CerPI]/([NBD\text{-}CerPI]+[NBD\text{-}Cer])) \times 100$$

Under the stated conditions, depending on the specific activity of the membrane preparation, 10–15% product was formed. The reaction profile in this range of product formation is in the linear portion of the reaction curve.

Example 4

Biotinylated Ceramide Reaction

2× master mix was prepared using the following recipe and with the following consituents:

| | |
|---|---|
| Biotin-$C_6$-ceramide | 2 µM |
| phosphatidylinositol (Sigma - soybean) | 0.05 mM |
| CHAPS | 2 mM |
| potassium phosphate buffer, pH 7.0 | 50 mM |
| Organic Co-solvent | up to 2.5% |
| (non-specific) protein concentration | 0.45 mg/ml |
| Final Volume | 50 µl |

To the above solution, 8.4 µl Biotin-$C_6$-ceramide (0.1 mg/ml in MeOH) and 35 µl phosphatidylinositol (1 mg/ml in $CHCl_3$) and tritiated phosphatyldylinositol (10 Ci/mmol) were added, and the product dried in vacuo.

The dried product was then redissolved by adding the following ingredients in the following order: 80 µl 20 mM CHAPS, 280 µl deionized water, 40 µl 0.5 M KPi buffer, pH 7.0 and sonicated for 5 minutes. This was considered "2× master mix".

Membrane stock was thawed and diluted to 1.8 mg/ml in 0.05 M KPi buffer, pH 7.0 and kept on ice.

Reaction Conditions

25 µl of 2× master mix was aliquoted into screw-cap microfuge tubes and kept at room temperature. 10 µl of 0.05 M KPi buffer pH 7.0 was added to each sample, followed by 2.5 µl of test compound or extract in 50% (max) organic co-solvent. The reaction was initiated by adding 12.5 µl of membrane stock to each reaction vessel, mixing, and incubating at room temperature for 2 hours.

Reactions were terminated by addition of a suspension of streptavidin-conjugated scintillation proximity beads (4 mg in 200 µl) and the mixture incubated with the beads with shaking for one hour at room temperature.

The radioactivity of the product was counted in a scintillation counter or in a microplate scintillation counter such as a Top-Count (Packard).

What is claimed is:

1. A method to determine the ability of a test compound to inhibit inositolphosphorylceramide (IPC) synthase, comprising:

recombinantly expressing the Saccharomyces IPC1 gene in a plurality of cells transformed to express said gene, said cells being in homogeneous culture and located in a container useful for addition of liquids; and introducing excess ceramide and phosphatidylinositol, said ceramide or phosphatidylinositol carrying label for identification, and test compound to said container; and subjecting said container and contents to ordinary conditions necessary for ceramide conversion to phosphoinositol ceramide; and identifying those test compounds which inhibit ceramide conversion to phosphoinositol ceramide.

2. The method of claim 1, wherein the IPC1 gene is over-expressed.

3. The method of claim 1, wherein the cells are chosen from the group consisting of: E. coli; S. cerevisiae and S. pombe.

4. A method of claim 1, wherein the labeled starting substrate is a $C_2$–$C_{12}$ ceramide.

5. A method of claim 4, wherein the $C_2$–$C_{12}$ ceramide is NBD-$C_6$-ceramide.

6. A method of claim 4, wherein the $C_2$–$C_{12}$ ceramide is BODIPY-C5-ceramide.

7. A method of claim 4, wherein the $C_2$–$C_{12}$ ceramide is N-hexanoyl-sphingosine.

8. A method of claim 4, wherein the $C_2$–$C_{12}$ ceramide is labeled with fluorescent material.

9. A method of claim 4, wherein the $C_2$–$C_{12}$ ceramide is labeled with a radioactive material.

10. A method of claim 9, wherein the radioactive material is chosen from the group consisting of: $^3$H and $^{14}$C.

11. A method to determine the ability of a test compound to inhibit IPC synthase, comprising:

recombinantly expressing the Saccharomyces IPC1 gene in a plurality of cells transformed to express said gene, said cells being in homogeneous culture and located in a container useful for addition of liquids; and introducing excess biotinylated ceramide, labeled phosphatidylinositol and test compound to said container; and subjecting said container and contents to ordinary conditions necessary for ceramide conversion; and conjugating said biotinylated ceramide to streptavidin-derivatized solid substrate; and identifying those test compounds which inhibit ceramide conversion to phosphoinositol ceramide.

12. A method of claim 11, wherein the solid substrate is a plurality of scintillation proximity assay (SPA) beads.

13. A method of claim 11, wherein the phosphatidylinositol is labeled with label selected from the group consisting of tritium and $^{32}$P.

14. A method to determine the ability of a test compound to inhibit IPC synthase, comprising:

recombinantly expressing the Saccharomyces IPC1 gene in a plurality of cells transformed to express said gene, said cells being in homogeneous culture and located in a container useful for addition of liquids; and introducing excess biotinylated ceramide, phosphatidylinositol and test compound to said container; and subjecting said container and contents to ordinary conditions necessary for ceramide conversion; and conjugating said biotinylated ceramide to labeled streptavidin-derivatized solid substrate capable of filter separation; and filtering to isolate the labeled streptavidin-derivatized solid substrate; and identifying those test compounds which inhibit ceramide conversion to phosphoinositol ceramide.

15. A method of claim 11, wherein the solid substrate is a plurality of SPA beads.

16. A method of claim 14, wherein the phosphatidylinositol is labeled with label selected from the group consisting of tritium and $^{32}$P.

17. A method to determine the ability of a test compound to inhibit IPC synthase, comprising:

introducing into a container that contains a plurality of untransformed cells that express IPC synthase, excess biotinylated ceramide, labeled phosphatidylinositol, and test compound; and subjecting said container and contents to ordinary conditions necessary for ceramide conversion to phosphoinositol ceramide; and identifying those test compounds which inhibit ceramide conversion to phosphoinositol ceramide.

* * * * *